United States Patent
Koros et al.

[11] Patent Number: 6,139,493
[45] Date of Patent: Oct. 31, 2000

[54] RETRACTOR WITH ADJUSTABLE LENGTH BLADES AND LIGHT PIPE GUIDES

[76] Inventors: Tibor B. Koros; Gabriel J. Koros, both of 610 Flinn Ave., Moorpark, Calif. 93021

[21] Appl. No.: 09/346,453

[22] Filed: Jul. 1, 1999

Related U.S. Application Data

[63] Continuation-in-part of application No. 09/112,024, Jul. 8, 1998, Pat. No. 5,928,139.

[51] Int. Cl.⁷ .................................................. A61B 17/02
[52] U.S. Cl. ......................... 600/215; 600/213; 600/231
[58] Field of Search .................................. 600/201, 205, 600/210, 215, 231, 232, 235, 245, 213

[56] References Cited

U.S. PATENT DOCUMENTS

| | | | |
|---|---|---|---|
| 1,157,202 | 10/1915 | Bates et al. | 600/215 X |
| 1,706,500 | 3/1929 | Smith | 600/232 |
| 2,474,857 | 7/1949 | Newman | 600/215 X |
| 3,384,078 | 5/1968 | Gauthier | 600/215 |
| 3,522,799 | 8/1970 | Gauthier | 600/215 |
| 3,626,471 | 12/1971 | Florin | 600/245 X |
| 3,965,890 | 6/1976 | Gauthier | 600/215 |
| 4,156,424 | 5/1979 | Burgin | 600/213 |
| 4,562,832 | 1/1986 | Wilder et al. | 600/245 X |
| 4,616,635 | 10/1986 | Caspar et al. | 600/215 |
| 5,027,793 | 7/1991 | Engelhardt et al. | 600/210 |
| 5,728,046 | 3/1998 | Mayer et al. | 600/215 X |
| 5,795,291 | 8/1998 | Koros et al. | 600/231 X |
| 5,928,139 | 7/1999 | Koros et al. | 600/215 X |

*Primary Examiner*—Paul J. Hirsch
*Attorney, Agent, or Firm*—David O'Reilly

[57] ABSTRACT

Variable length blades for use with a retractor or distractor include a fixed upper portion and an adjustable extension that allows adjustment to accommodate a wide range of patients. A variable length retractor blade has a fixed upper portion that can vary in length from 10 to 15 cm. having a telescoping extension that can be adjusted to vary the length of the blade from 12 to as much as 24 cm. The variable blades include conventional flanges with a header for securing the variable blades on the end of retractor/distractor arms. An additional option is the inclusion of tubular guides in the variable length blade extension for placement of plurality of fixation screws and a light pipe to provide intensive illumination for the surgical site. Three tubular guides are provided in the upper and lower ends of the telescoping extension on the variable length blade for use with a distractor. The two outer tubular guides are used to place two fixation grooves in each blade to provide a stable platform for a distractor frame. A center tubular guide is used to position a light pipe for intense illumination of a surgical site. A locking mechanism is also provided to hold a telescoping extension in an adjusted position. The locking mechanism is comprised of teeth along one edge of the fixed blade and a ratchet mechanism to lock the position of a blade after it is extended.

13 Claims, 6 Drawing Sheets

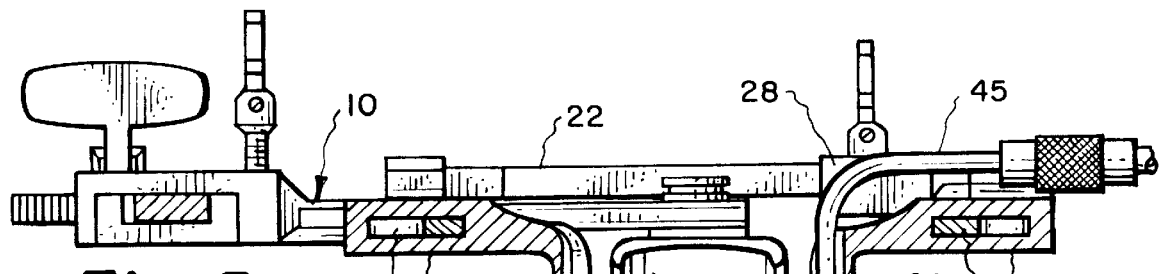
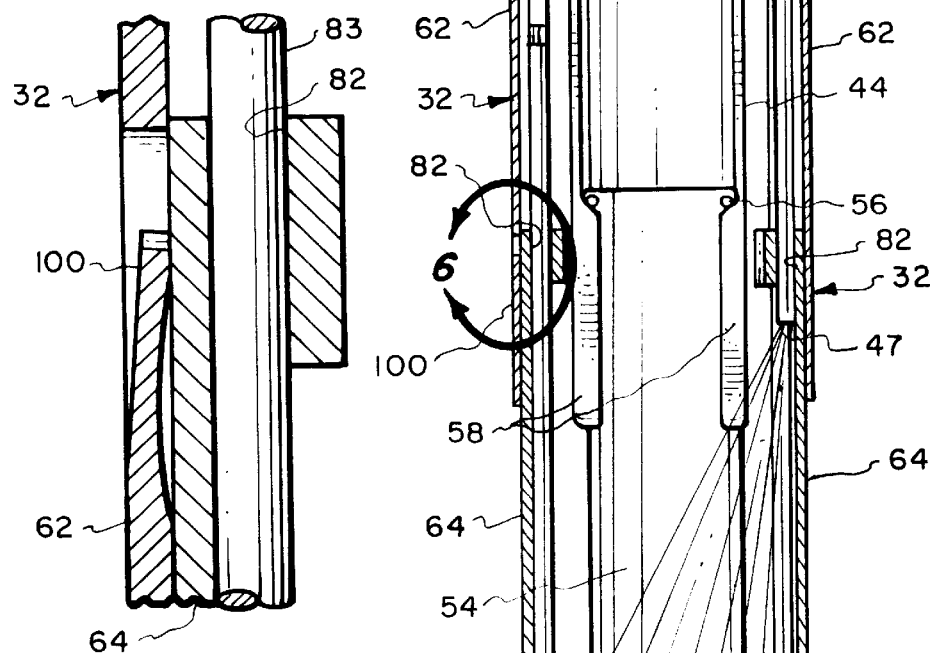
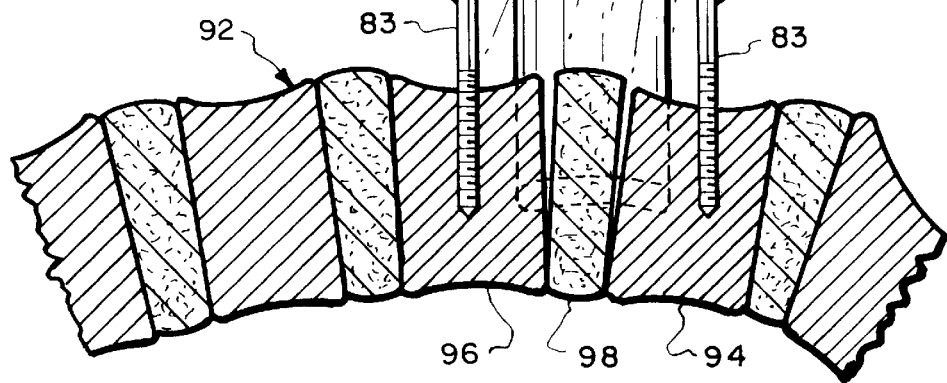

RETRACTOR WITH ADJUSTABLE LENGTH BLADES AND LIGHT PIPE GUIDES

This application is a Continuation-In-Part application of prior application Ser. No. 09/112,024, now U.S. Pat. No. 5,928,139 filed Jul. 8, 1998.

BACKGROUND OF THE INVENTION

1. Field of the Invention

This invention relates to retractors used in surgical procedures and more particularly relates to a retractor for lumbar spinal fusion that includes adjustable length retractor blades and guides for positioning fixation screws and a light pipe.

2. Background Information

In a surgical procedures trauma to the patient and damage to the tissue needs to be minimized as much as possible. To achieve this result surgeons try to keep incisions as small as possible when performing surgical procedures such as lumbar spinal fusions by making a midline mini-incision. However, it is necessary that the surgeon performing the delicate surgery to have a clear view of the operating field. A variety of retractors are available to keep an incision open and provide a clear view of the field of the operation.

Such surgical retractors are particularly important in performing spinal fusions, and particularly lumbar disc operations where the surgical procedure is provided by an anterior/lateral approach through the abdomen. One such retractor is disclosed and described in U.S. patent application Ser. No. 08/935,761, now U.S. Pat. No. 5,944,658 of T. Koros et al filed Sep. 23, 1997 and incorporated herein by reference. This application discloses a retractor in which the surgeon makes a small incision in the abdomen to view the region of the vertebrae where the lumbar disc operation is to be performed. The retractor disclosed is inserted in the incision to hold organs, muscles, arteries and other tissue out of the way and provide a clear view of the spinal region being operated on.

Another important feature of the retractor is allow insertion of retractor blades without damage to the tissue. To achieve this the lumbar spinal fusion retractor and distractor system of the above mentioned application is constructed to displace only a small volume when inserted in the incision before it is opened, or "spread" to provide a clear view of the operating field.

Another important feature of the retractor is that it stay in position in the difficult lumbar fusion. To prevent such occurrences, fixation screws are provided that pass through blades of the retractor and are fastened to adjacent vertebra.

However, another common problem with this retractor is that no single length of blade that is suitable for all patients. Therefore several different size blades must be provided for different patients. This requires up to at least twelve different blades being provided and sterilized for an operation. The size and length of the blades can vary anywhere from 10 cm to 24 cm. Also when the retractor is placed in the patient, the surgeon may have to experiment with different length blades until he gets the right length. This increases the length of the operation and the danger of increased trauma to the patient. It would be advantageous if a single blade could be used having a length adjustment allowing rapid positioning and placement.

Another important aspect of the retractor is the provision of viewing an extremely small area during this surgical procedure to minimize the size of the incision. Thus it is apparent that a very clear view of the operating site must be provided. To accomplish this light pipes are used on the end of long cables that provide intense illumination of the surgical site. Since the volume of the area being operated on is small, the inclusion of a light pipe in the patient creates additional problems of interference with the surgical procedure.

It would therefore be advantageous if a method could be provided to accommodate a light pipe and providing intense illumination while avoiding interference with the surgical procedure.

It is therefore one object of the present invention to provided an improved retractor having retractor blades that are adjustable in length.

Still another object of the present invention is to provide a retractor with an adjustable length blades that remain fixed at an adjusted position.

Still another object of the present invention is to provide a retractor having an adjustable length blades having guides for fixation screws for attaching the retractor to the vertebrae of the patient.

Still another object of the present invention is to provide a retractor having adjustable length retractor blades with stops to prevent the adjustable length blades from being dislodged from the retractor.

Yet another object of the present invention is to provide a retractor having adjustable length retractor blades that are held in place at their adjusted position by frictionally engaging leaf springs.

Yet another object of the present invention is to provide adjustable length adjustable blades having a guide for receiving and holding a light pipe.

Yet another object of the present invention is to provide a retractor having adjustable length blades with guides for attaching multiple fixation screws to vertebra.

Other objects and advantages of the invention will become more apparent from the following portion of this specification, and the accompanying drawings.

BRIEF DESCRIPTION OF THE INVENTION

The purpose of the prevent invention is to provide an improved retractor such as a lumbar fusion laminectomy retractor and distractor that has adjustable length blades and guides for accommodating a plurality of fixation screws and a light pipe.

The lumbar fusion retractor and distractor of the present invention is comprised of a retractor frame each having a stationary arm on the end of the crossbar having a rack gear and a movable arm that includes a crank mechanism. For a lumbar fusions a retractor frame and a distractor frame are provided. The movable arm on each of the frames is adjustable along the rack gear along the crossbar by a crank mechanism disclosed and described in U.S. Pat. No. 5,167,223 issued Dec. 1, 1996 to T. Koros et al and incorporated herein by reference.

The movable arm is movable along the rack gear of the crossbar for fine adjustment by the crank mechanism comprised of a pinion gear engaging the rack gear turned by a foldable crank handle that closes and opens the parallel arms. The retractor and distractor frames, with folded crank arms, provide a low profile to minimize interference with the surgeon performing the surgical procedure.

For lumbar fusion surgical procedures a pair of retractor frames known as a retractor and distractor are provided. The distractor includes fixation screws to allow adjacent vertebrae to be spread by the distractor. With two retractor frames (i.e., a retractor and distractor) the retractor blades surround the surgical site providing a clear view to the surgeon. With the retractor/distractor disclosed in U.S. patent application Ser. No. 08/935,761, now U.S. Pat. No. 5,944,658 disclosed hereinabove the blades are first positioned in the incision around the surgical site and with a clamp handle the clamps on each retractor blade to manual insert and position of the blade. Depending upon the patient's anatomy several different length blades may be tried before the appropriate length is selected. Two of the blades are attached to adjacent vertebrae by fixation screws. The retractor and distractor frames then engage the blades and are retracted by operating the crank mechanisms to spread the retractor and the incision to provide a clear view of the surgical site. The non-fixed blades may be tilted to provide a wider field of view as described in the prior application referred to hereinabove.

The present invention avoids the need for up to 12 or more different blades by providing variable length blades. While the variable length blades of the invention are described with respect to the retractor/distractor system for lumbar fusions, they of course can be attached to any retractor for use in any abdominal surgery.

The variable length retractor blades are comprised of a blade having flanges or edges on either side providing channels for receiving a telescoping blade extension. The variable length blade is thus comprised of two pieces; an upper fixed length portion having channels for receiving a lower adjustable portion or extension which telescopes into the upper portion. Thus a single blade can cover a wide range of depths from about 10 cm to about 18 cm. For longer blades up to 24 cm. a second variable length blade will be provided. A single blade can cover a nominal depth of up to 24 or 25 cm. and would have a closed length of approximately 14 to 15 cm. To cover depths of less than 14 cm. a second variable length blade can be provided that would cover a range of 10 to about 18 cm.

The telescoping extension on the variable length retractor blades has a slightly curved shaped and it includes stops at the upper end of the extension to prevent the lower portion from becoming detached. An optional but preferred feature is inclusion of frictionally engaging integrally formed leaf springs that frictionally press against the telescoping extension to hold it at whatever position it may be set. The blade itself and the extension are substantially smooth somewhat curved shaped similar to standard blades.

In another optional but preferred embodiment the blades include tubular guides for fixation screws and a light pipe. In this embodiment the tubular guides are formed in the upper and the lower ends of the variable retractor blade extension. Preferably there are three tubular guides allowing attachment by a pair of fixation screws and a third tubular bore or guide for receiving a light pipe.

The retractor/distractor frame disclosed and described in U.S. patent application Ser. No. 08/935,761 now U.S. Pat. No. 5,944,658, filed Sep. 23, 1997 discloses a blade having a single centrally located channel slot for receiving a single fixation screw. However it has been discovered that additional fixation screws are preferred to provide added stability. For that reason the variable length extendible blade of the present invention provides at least two tubular guides for fixation screws that can be spaced apart approximately the width of the blade. A third tubular guide is provided for receiving and holding a light pipe to illuminate the surgical site.

As in the prior application referred to hereinabove the lumbar retractor/distractor system is carefully positioned by first placing the variable length blades in the incision on opposite sides of the spine, chosen according to patient's requirement. With the extendible blades the length of the blade can be adjusted to the depth required. The longer variable length would be extendible from approximately 14 to 15 cm. to up to 24 or 25 cm. If a shorter blade is needed a second pair of extendible blades can be provided. Thus the present invention reduces the number of blades that must be kept available from at least twelve to no more than four and possibly only two. The blades are positioned by clamping a handle on a retractor blade having a boss or header for receiving clamp. This allows the blade to be manually inserted in the incision and positioned adjacent to surgical site.

After the hand retraction by manually placing the variable length blades the retractor frames are introduced with the blades properly positioned, or placed in a standard mid-line incision. The retractor frames are comprised of a crossbar, having a rack gear and a pair of arms attached to the crossbar. One retractor arm is stationary at the end of the crossbar while the other arm is movable to open or close the retractor arms to spread the incision.

The retractor arms are positioned fully closed between the heads of the retractor blades and cranked open until the extendible blades become engaged with notches or slots in the end of the retractor arms. The retractor arms are then opened until the desired retraction is achieved and a clear view of the operating site is obtained. The heads of the blades self-engage and self-lock in the slots at the end of the retractor arms and are held firmly in place by tissue pressure. The clamp handle used to manually positioning the blades may then be removed.

With a clear view of the operating site by the position of the variable length retractor blades and open retractor arms spreading the incision a distractor at right angles to the retractor can be introduced. The variable length distractor blades having tubular guides for fixation screws are carefully placed in the incision in the cephalat-ciudad direction with clamp handles as before. Instead of a single screw in the invention described in the patent application referred to hereinabove, a pair of screws can be slid down the pair of tubular guides and then screwed into adjacent vertebrae on opposite sides of the diseased lumbar disc. Usually pilot holes will be drilled in the vertebrae to ease the insertion of the fixation screws.

A third tubular channel between the outer tubular channels is provided to receive a right angle light pipe that provides intense illumination of the surgical site. Once the variable length blades are positioned and pinned in place by the fixation screws the second offset frame can be introduced to engage the heads of the variable length distractor blades. The adjacent vertebrae can then be gently spread by cranking the right angle offset distractor frame to spread the firmly attached distractor.

If the variable length blades are used with the retractor frame of the patent application described hereinabove the field of view can be widened by using the tilt mechanism to spread the tips of the blades to retract the surrounding tissue without enlarging the incision. When in this final position the surgeon has now a clear, lighted view of the lumbar disc region. The sequence of installing retractor and distractor blades and frames, of course, may vary. Further the variable length retractable blades shown and described in this application can be used with other retractor frames that have conventional retractor arms for receiving the heads of the blades.

Another optional but preferred feature of the invention is the inclusion of a lock mechanism to fix the adjusted position of the blades so they will not move during an operation. In the previous embodiments the blade is adjusted and held in place by friction. However, they are not secured against any movement. In this embodiment a ratchet-type mechanism in the form of teeth along one edge of the blade secured by a pawl having a catch fixes the adjusted position of the blade. The pawl is spring loaded and remains in place holding the blade in an adjusted position. The teeth are constructed with a cam or oblique surface on one side and a right angle surface on the other. This allows extension or lengthening of the blade without releasing the pawl. During an operation the surgeon may adjust the length of the blade by manually extending the lower telescoping section of the blade. The pawl and catch engage one of the teeth along the edge of the blade and lock the blade in the extended position. To shorten the blade the pawl and catch are released by pressing on a lever allowing the telescoping blade extension to be retracted.

The above and other novel features of the invention will be more fully understood from the following detailed description and the accompanying drawings, in which:

BRIEF DESCRIPTION OF THE DRAWINGS

FIG. 5 is a sectional view of the retractor/distractor system with the variable length blade taken at 5—5 of FIG. 4.

FIG. 6 is a partial sectional view taken at 6 of FIG. 5 illustrating the adjustment restraining system for the variable length blade telescoping extension.

DETAILED DESCRIPTION OF THE INVENTION

Figure 1:
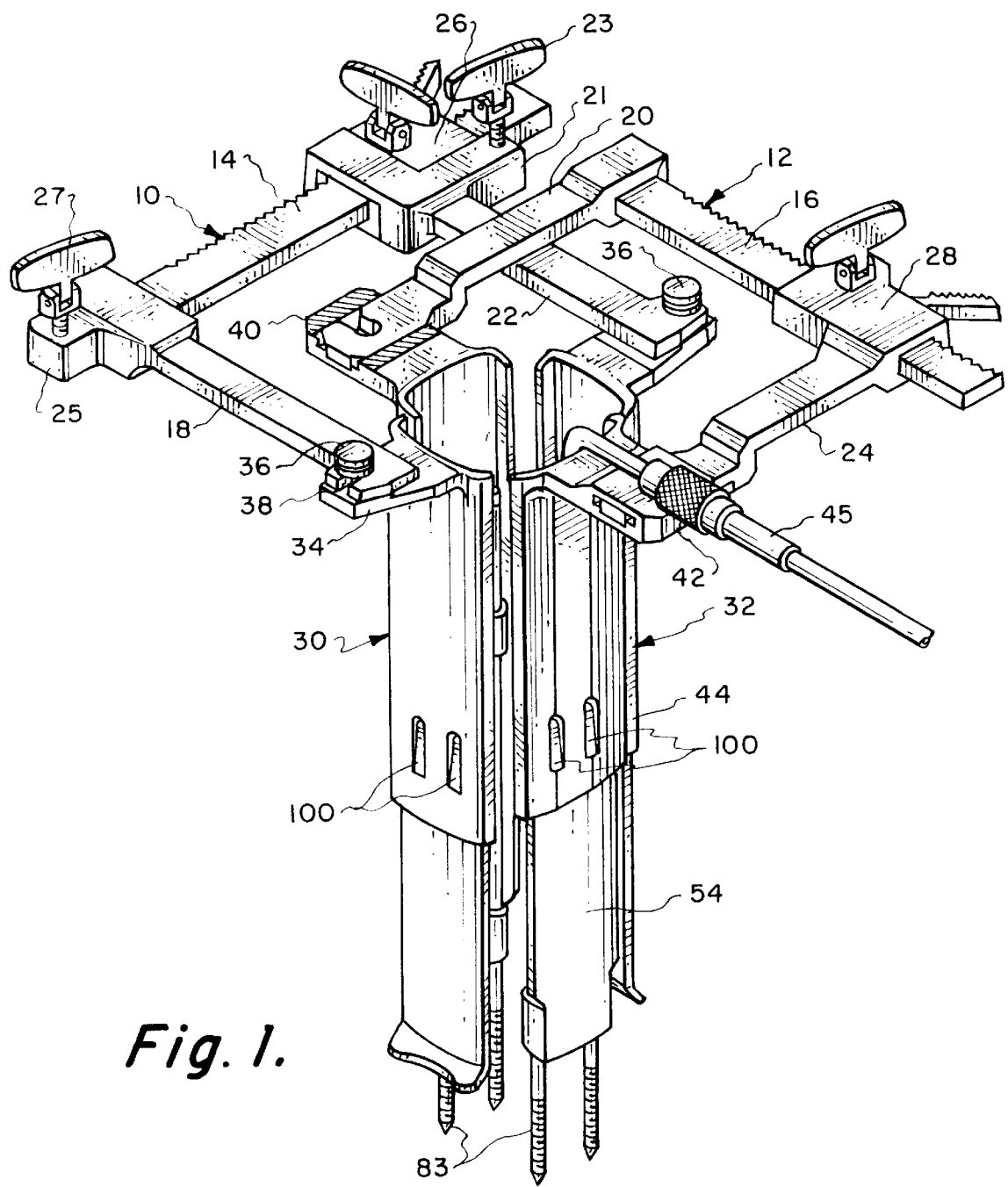
FIG. 1 is an isometric view of a retractor/distractor system using variable length telescoping blades according to the invention.

A retractor/distractor system similar to that shown and described in U.S. patent application Ser. No. 08/935,761 now U.S. Pat. No. 5,944,658 filed Sep. 23, 1997 by T. Koros et al is shown in generally in FIG. 1. The retractor/distractor system is comprised of a retractor 10 and a distractor 12 each comprised of frames 14 and 16 respectively having stationary arms 18 and 20 and movable arms 22 and 24. Movable arms 22 and 24 are movable by crank mechanisms 26 and 28 as described in the above identified application incorporated herein by reference. Also included in this application is the tilt mechanism for tilting the non-fixed retractor blades described in the above-identified application.

An improvement to the retractor/distractor system is provided by variable length retractor blades 30 and variable length distractor blades 32. Variable length retractor blades 30 have a flange 34 with a boss or head 36 that engages a slot 38 in stationary arm 18 and movable arm 22. Likewise distractor variable length blades have flanges 40 and 42 with slots for receiving the ends of stationary arm 20 and movable arm 24.

Figure 2:
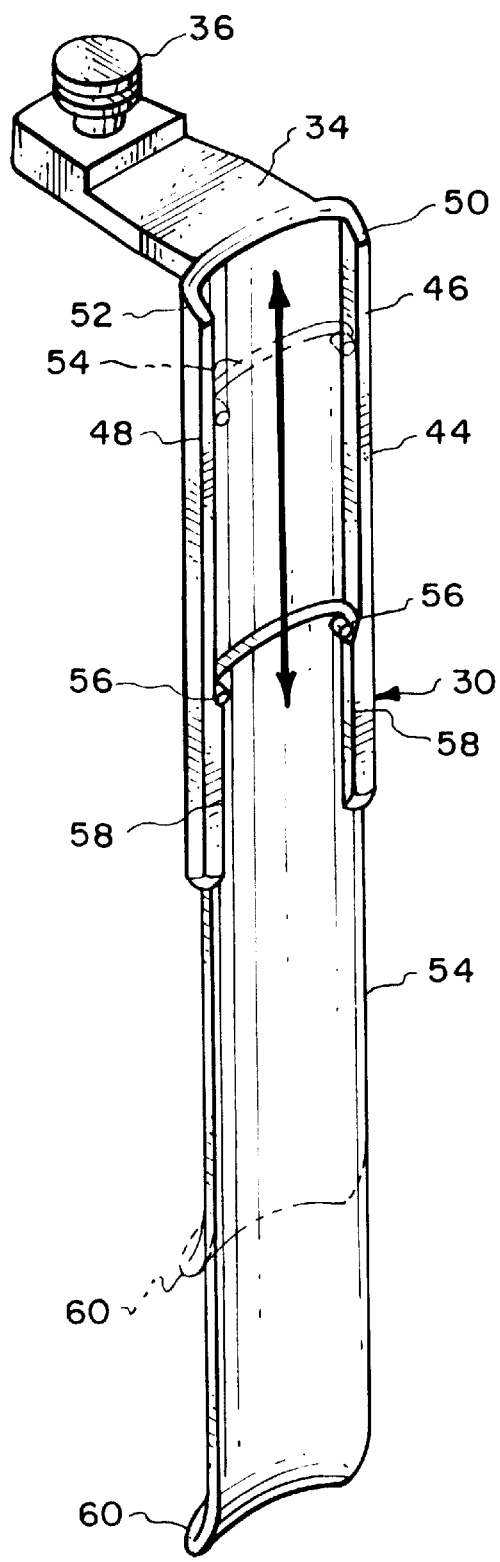
FIG. 2 is a perspective view of a plain variable length retractor blade having a telescoping extension.

The versatility of the retractor/distractor system is improved by the variable length telescoping blades which reduce the number of blades used for this system to no more than four. The variable length retractor/distractor blades 30 and 32 are shown in greater detail in FIGS. 2 and 3. Variable length retractor blade 30 has a flange 34 with a header or boss 36 for engagement by arms of the retractor after placement by a clamp handle (not shown). Previously retractor blades varying in length from 10 cm. up to about 25 cm. in at least four different sizes were required. The result is that for retractor 10 at least eight blades had to be sterilized and prepared for each operation. With improvement of the present invention one or at most two variable length retractor blades 30 are sufficient.

Variable length retractor blade 30 is comprised of an upper fixed retractor blade 44 having flanges 46 and 48 channels 50 and 52 for slidably receiving telescoping blade extension 54. Blade extension 54 is retracted or extended by sliding it downward or upward in channels 50 and 52. Stops are provided by studs 56 on each side of the blade that abut shoulders 58 formed on flanges 46 and 48. This prevents blade extension 54 from sliding out of fixed blade 44. The end of blade extension 54 has the usual curled end 60 to assist in holding tissue away from the surgical site.

Two sizes of variable length retractor blades should be sufficient to cover the range necessary. One size would be in a range of from about 10 to 12 cm. in a retracted position to about 18 cm. in an extended position. The total range of coverage would be from about 10 cm to about 25 cm. A second variable length blade would have a retracted length of approximately 14 to 15 cm. and an extended length of up to 24 to 25 cm. Thus variable length retractor blades for the retractor used in the lumbar fusion retractor/distractor system in FIG. 1 would be no more than four.

Figure 3:
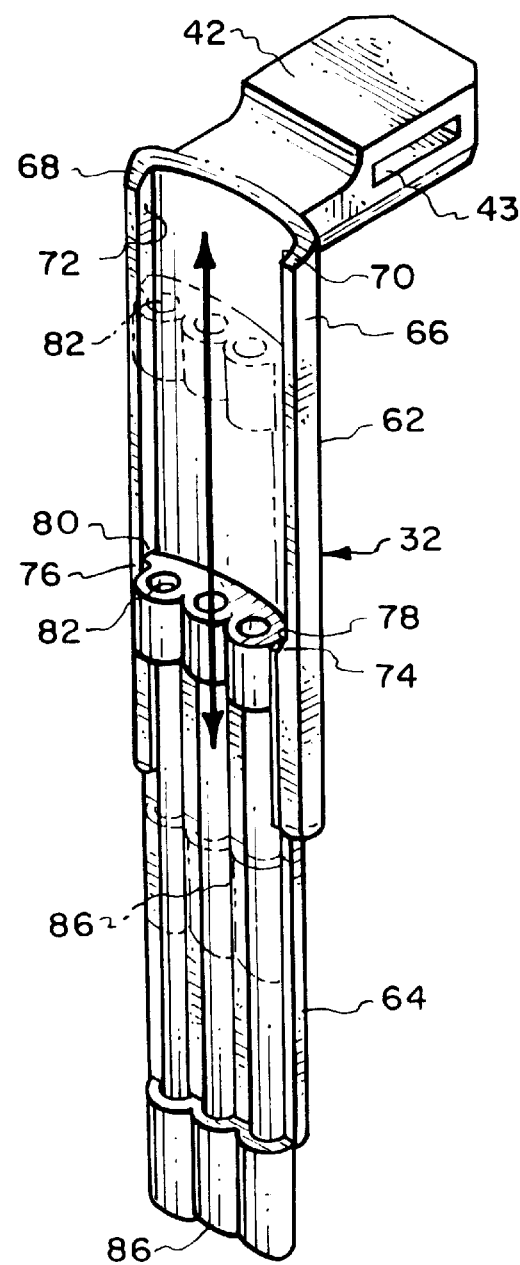
FIG. 3 is a perspective view of a second embodiment of a retractor variable length blade including tubular guides for mounting a plurality of fixation screws and a light pipe.

Variable length distractor blade 32 for use with fixation screws is illustrated in FIG. 3. Variable length distractor blade 32 has flange 42 having socket 43 for receiving the end of the fixed distractor arm 20 and movable distractor arm 24 as described previously. Variable length distractor blade 32 is comprised of fixed upper portion 62 and telescoping blade extension 64. Fixed blade portion 62 has flanges 66 and 68 forming channels 70 and 72 for receiving telescoping blade extension 64. The lower portion of flanges 66 and 68 are provided with shoulders 74 and 76 for engaging stops or studs 78 and 80 on the upper end of the blade extension 64 to prevent the blade from slipping out of fixed portion 62.

Distractor blades for use in lumbar fusion described in the patent application referred to hereinabove include a channel or slot for receiving a single fixation screw. However it has been discovered that additional fixation screws would be advantageous to provide stability and improve support for the distractor system. Thus telescoping blade extension 64 of the present variable length blade 32 is provided with tubular guides 82 at the top of blade extension 64 and aligned tubular guides 86 at the bottom end of variable extension 64.

The outermost guides of tubular guides 82 and 86 can support a pair of fixation screws 83 for each variable length distractor blade. The third or center tubular guide can be used to support a light pipe 45 providing intense illumination to the surgical site without interfering with the surgical procedure.

Figure 4:
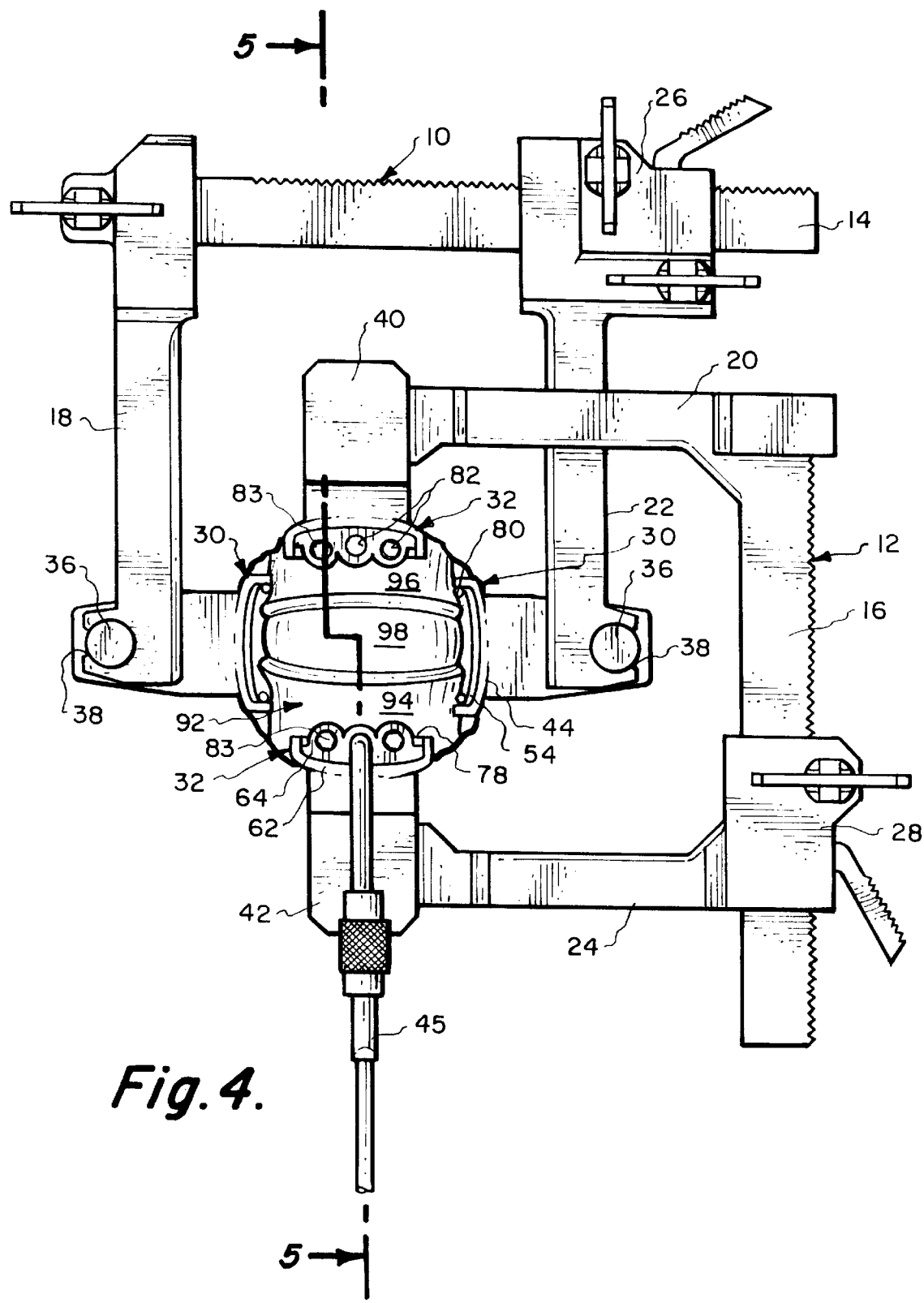
FIG. 4 is a top view of the retractor/distractor system placed in an incision for a clear view of the surgical site.

The installation and operation of the invention is illustrated in FIGS. 4 through 6. Variable length retractor blades 30 are carefully placed in an incision by a clamp handle traverse to spine 92. Telescoping blade extension 54 may then be adjusted to a length sufficient to retract the tissue adjacent to each side of spine 92. Retractor frame 10, in a fully closed position, is then placed between retractor blade heads 36 and opened by operating crank mechanism 26 until notches 38 engage the end of the retractor blades. The clamp handle may then be removed and retractor 10 opened further by turning the crank handle until the desired retraction of the incision is obtained.

Offset distractor frame 12 is then positioned in the incision with fixation screws 83 screwed into vertebrae 94 and 96 of spine 92 on opposite sides of affected disc 98. Fixation screws 83 firmly hold offset retractor frame in position allowing adjacent vertebrae 94 and 96 to be spread providing a clear view of the operating site.

The visibility of the operating site is substantially improved by a light pipe 45 inserted in tubular guide 82 as shown in FIG. 5. Light pipe 45 bends at a 90° angle over flange 42 of variable length distractor blade 32 and engaged tubular guide 82 between the tubular guides holding fixation screws 83. As described previously two fixation screws 83 are inserted through tubular guides 82 and 86 at the upper and lower end of variable length blade extension 64 and screwed into adjacent disc 94 and 96. Pilot holes may be drilled in each disc 94 and 96 for placement of fixation screws. Light pipe 45 is then placed in tubular guide 82 between fixation screws 83 in one of the adjustable length distractor blades 32. Light emitted from end 47 of light pipe 45 provides intense, clear illumination of the disc 98 being operated on.

Each telescoping extension in variable length retractor/distractor blades 30 and 32 is firmly held in an adjusted position by an integrally formed leaf spring 100 illustrated in the partial sectional view of FIG. 6. Leaf spring 100 is integrally formed in the upper fixed portion 62 of variable distractor blade 32 and presses firmly against blade extension 64 holding it in its adjusted position by friction. Preferably there are two such leaf springs in each variable distractor blade 32 and similar leaf springs 100 in variable length retractor blade 30.

With the distractor in place as illustrated in FIGS. 4 and 5 distractor arms 20 and 24 may be spread by operating crank mechanism 28 to spread vertebrae 94 and 96. This permits the surgeon to efficiently operate on affected disc 98.

Figure 7:
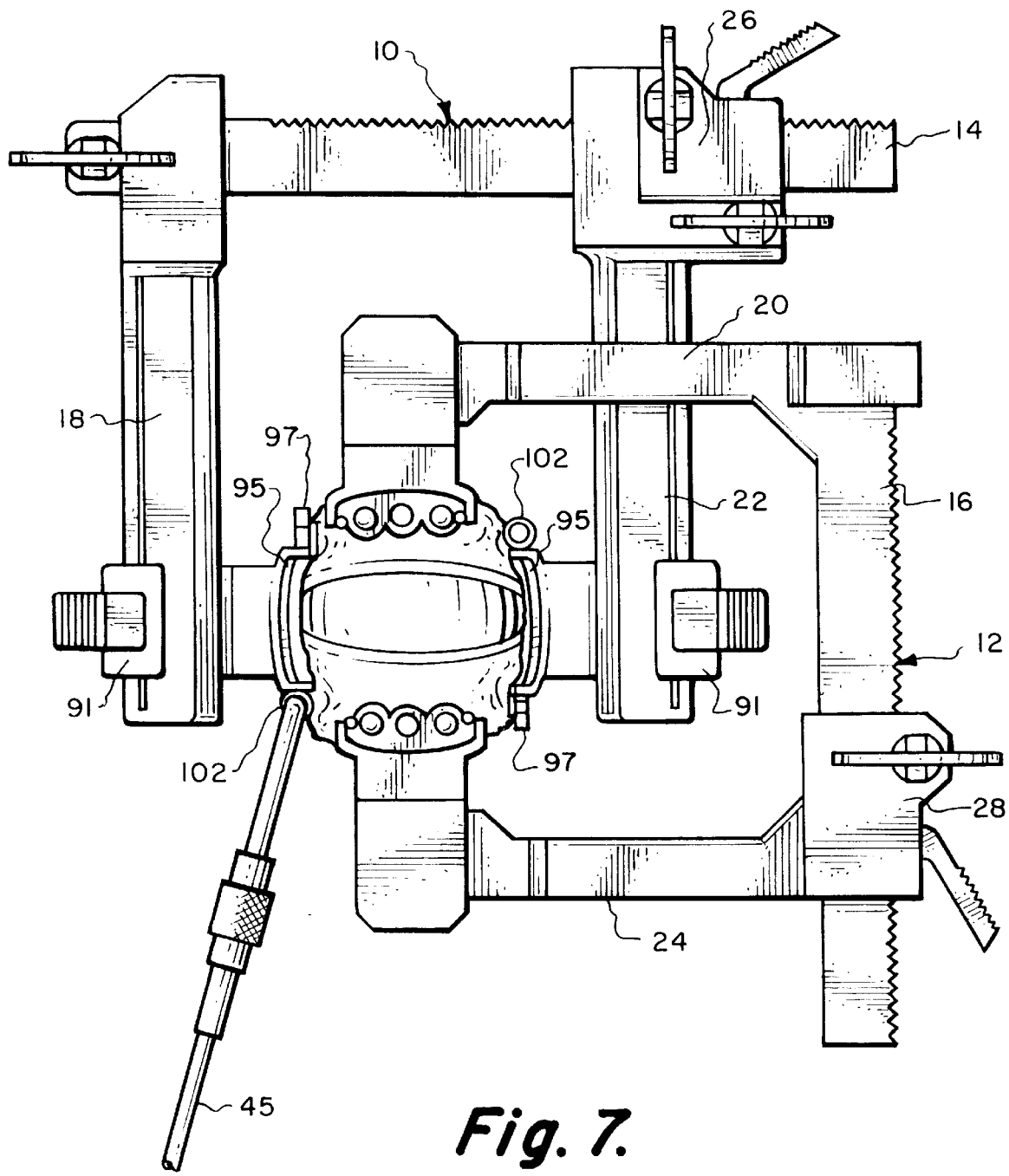
FIG. 7 is a top view of an alternate embodiment of the retractor/distractor system having a locking mechanism for fixing the adjusted position of the blades.
Figures 8, 9:
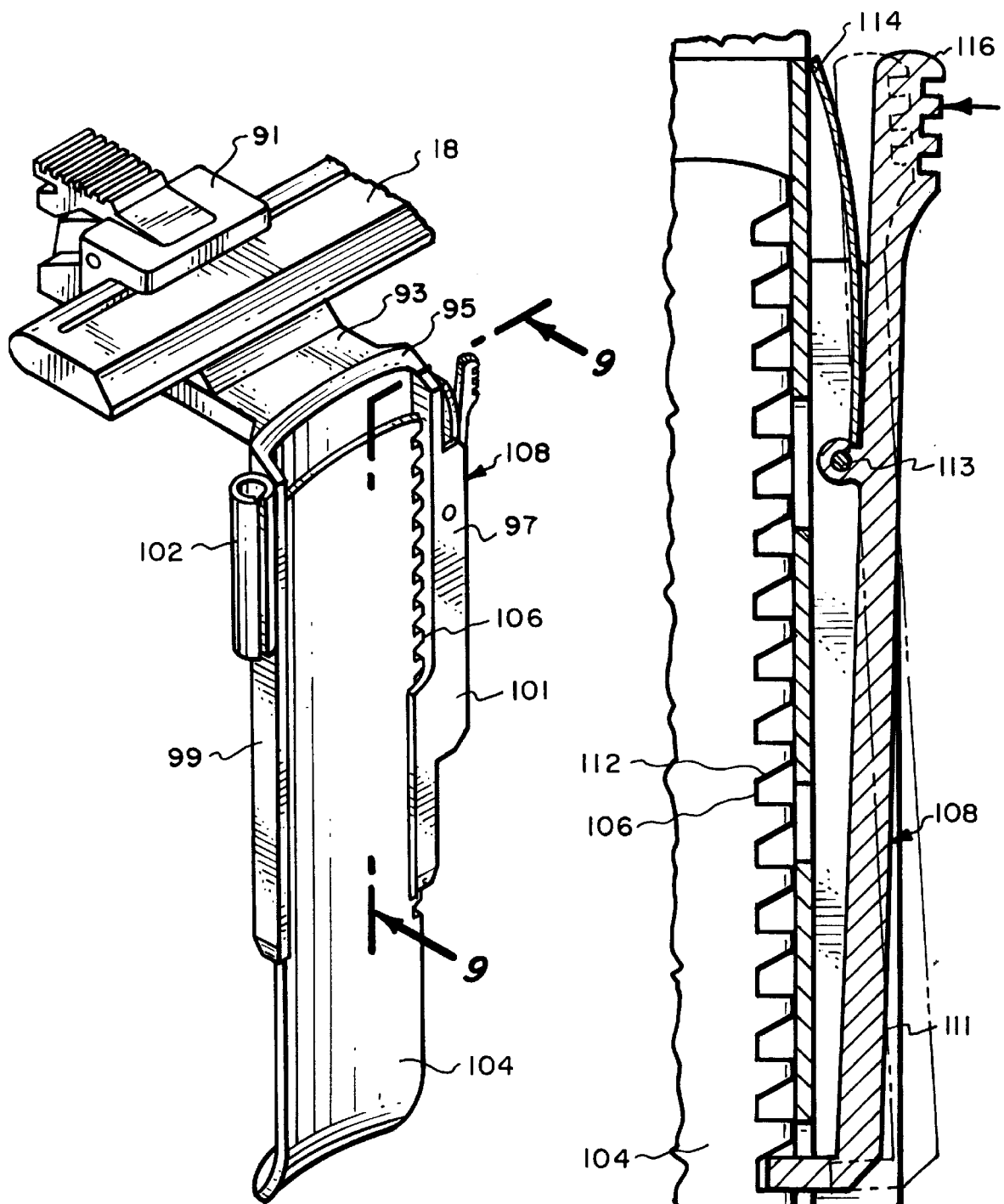
FIG. 8 is a perspective view illustrating the blade locking mechanism for fixing the adjustment position of the blade.
FIG. 9 is a sectional view taken at 9—9 of FIG. 8.

Another optional but preferred feature of the invention is the inclusion of a locking mechanism for the telescoping extension in the variable length retractor/distractor blades that securely holds the blades in a fixed, extended position after adjustment. This embodiment is illustrated in FIGS. 7 through 9. In this embodiment, this system is comprised of retractor 10 and distractor 12 each comprised of frames 14 and 16, respectively, having stationary arms 18 and 20 and movable arms 22 and 24 as before. An optional embodiment and improvement to the retractor/distractor system is provided by variable length retractor blades 95 having a locking mechanism which will be described in greater detail hereinafter.

Variable length retractor blades 95 are mounted on stationary or fixed arms 18 and 22 by retractor clamps 91. A locking mechanism 97 is provided for each variable length retractor blade 95 shown in greater detail in FIGS. 8 and 9.

Variable length retractor blade 95 is attached to retractor clamp 91 by flange 93 for securing the variable length blades to fixed arm 18 or 22. Variable length retractor blade 95 has flanges 99 and 101 and light guides 102 fixed or secured to flanges 98 and 100. Flanges 99 and 101 form channels for slidably receiving telescoping blade extension 104. Blade extension 104 is extended or retracted by sliding it downward or upward in channels formed by flanges 99 and 101.

However, a more positive locked adjusted position is provided by locking ratchet mechanism 97 comprised of a rack gear or teeth 106 along one edge of telescoping blade extension 104 and a spring loaded pawl 108 having a tongue or catch 110 for positively locking the adjusted position of blade 104. Pawl 108 is formed of elongate lever 111 pivotally mounted on flange 101 by pivot pin 113 having catch 110 on one end and finger pad 113 on the other. Leaf spring 114 between pivot pin 113 and the side of flange 101 biases catch 110 into teeth or gear rack 106. Ratchet teeth or gears 106 along the edge of telescoping blade extension 104 have an oblique side 112 forming a cam that allows telescoping blade extension 104 to be extended without releasing pawl 108 but requires release of catch 110 from teeth 106 to retract blade extension 104. Leaf spring 114 pivots and holds catch 110 in position against teeth 106. Pawl 108 is released by pressing finger pad 116 on lever 111 to release catch 110 from rack gear or teeth 106.

Thus in operation variable length blade 95 may be extended by pushing or pulling down on telescoping blade extension 104 allowing catch 110 to slide on oblique surfaces 112 until an adjusted position is obtained. Catch 110 on pawl 108 will then lock telescoping blade extension 104 in extended, adjusted position. Leaf spring 114 holds pawl 108 with catch securely in teeth 106. To retract telescoping blade extension 104 pressure on finger pad 116 detaches catch 110 on pawl 108 from teeth 106 allowing blade extension 104 to be retracted.

Light pipe guides 102 attach to flanges 99 and 101 on variable blade 95 is provided for insertion of light pipe 45 as before. Thus light can be provided on either side of the incision by insertion of light pipe 45 in one or the other of light pipe guides 102 on variable length blades 95. Optionally a light pipe could be inserted in both light guides 102.

The retractor/distractor system with variable length adjustable blades 30 and 32 also includes the tilt mechanism disclosed and described in U.S. patent application Ser. No. 08/935,761 now U.S. Pat. No. 5,944,658 referred to hereinabove and incorporated by reference. After placement of the retractor/distractor in the incision the field of view can be improved by tilting non-fixed variable length retractor blades 30 by operating tilt mechanisms 21 and 25. Tilt mechanisms 21 and 25 are adjusted by operating tilt crank handles 23 and 27 as described in the above identified application. The use of variable length adjustable blades in combination with the tilt mechanism substantially increases the versatility of the retractor/distractor system.

Thus there has been described a unique, novel variable length retractor/distractor blade that reduce the number of blades necessary for surgical procedures. Variable length retractor blades are disclosed having an adjustable telescoping extension slidably mounted in a fixed upper portion of the retractor blade that is held in adjustable position by integrally formed leaf springs. A conventional flange and header on the blade is provided for placement by a clamp and engagement by ends of retractor arms. Similar distractor blades are disclosed having an adjustable telescoping extension that include tubular guides for fixation screws as well as an additional guide for receiving a light pipe to intensely illuminate a surgical site. While the variable length retractor and distractor blades are described for use with a lumbar fusion retractor/distractor system they obviously may be used for other surgical procedures and are constructed with flanges that will fit other conventional retractor arms. The variable length retractor/distractor blades of the present invention provide a unique feature of minimizing the number of blades needed for a particular surgical procedure from twelve or more down to about four.

This invention is not to be limited by the embodiment shown in the drawings and described in the description which is given by way of example and not of limitation, but only in accordance with the scope of the appended claims.

What is claimed is:

1. A variable length blade for a surgical retractor comprising;
   a fixed blade having longitudinal flanges forming channels;
   means for securing said fixed blade to a retractor arm;
   an extendible blade, said extendible blade telescopically engaging said longitudinal channels for retraction into or extension from said fixed blade to adjustably vary the length of said variable length blade;
   blade restraining means for restraining and holding said extendible blade in an adjusted position;
   said blade restraining means including locking means for locking said extendible blade in an extended position;
   said locking means comprising a plurality of teeth along an edge of said extendible blade and a pawl pivotally mounted to said fixed blade and having a catch for engaging said teeth to lock said extendible blade in a predetermined extended position;
   whereby said variable length retractor blade can be adjusted and re-adjusted for use on a wide range of surgical procedures.

2. The variable length blade according to claim 1 including means for preventing said telescopically extendible blade from disengaging from said fixed blade.

3. The variable length blade according to claim 2 in which said means for preventing said extendible blade from disengaging comprises; stop means on said extendible blade.

4. The variable length blade according to claim 3 in which said stop means comprises; at least one stud on said extendible blade.

5. The variable length blade according to claim 4 in which said at least one stud comprises a pair of studs.

6. The variable length blade according to claim 5 in which said stop means includes; terminating means terminating said channels in said longitudinal flanges.

7. The variable length blade according to claim 6 in which said terminating means comprises a shoulder formed on said longitudinal flanges; said pair of studs engaging said shoulders.

8. The variable length blade according to claim 1 in which said pawl comprises; an elongate lever pivotally attached to said fixed blade; said catch being formed at one end of said elongate lever; spring means biasing said elongate lever to hold said catch in engagement with said teeth until released.

9. The variable length blade according to claim 8 including means to allow said extendible blade to be extended without releasing said catch.

10. The variable length blade according to claim 9 in which said means to allow said extendible blade to be extended without releasing said catch comprises; an oblique cam surface formed on an upward side of said teeth on an edge of said extendible blade.

11. The variable length blade according to claim 1 including tubular light guide means on said variable length blade.

12. The variable length blade according to claim 11 in which said tubular light guide means comprises a tubular light guide socket attached to an edge of said fixed blade for receiving a light pipe.

13. The variable length blade according to claim 12 in which there are two tubular light guides with one attached to each side of said fixed blade.

* * * * *